US007910122B2

(12) United States Patent
Sirinyan et al.

(10) Patent No.: US 7,910,122 B2
(45) Date of Patent: Mar. 22, 2011

(54) ACTIVE COMPOUND-CONTAINING SOLID MOULDED BODIES FOR EXTERNAL USE AGAINST PARASITES ON ANIMALS

(75) Inventors: Kirkor Sirinyan, Bergisch Gladbach (DE); Reinhold Löhr, Bergisch Gladbach (DE)

(73) Assignee: Bayer Animal Health GmbH (DE)

( * ) Notice: Subject to any disclaimer, the term of this patent is extended or adjusted under 35 U.S.C. 154(b) by 822 days.

(21) Appl. No.: 11/631,089

(22) PCT Filed: Jun. 16, 2005

(86) PCT No.: PCT/EP2005/006465
§ 371 (c)(1),
(2), (4) Date: Aug. 3, 2007

(87) PCT Pub. No.: WO2006/000335
PCT Pub. Date: Jan. 5, 2006

(65) Prior Publication Data
US 2008/0292672 A1    Nov. 27, 2008

(30) Foreign Application Priority Data

Jun. 29, 2004   (DE) .......................... 10 2004 031 325

(51) Int. Cl.
*A01N 25/10*    (2006.01)
(52) U.S. Cl. ........ 424/411; 424/405; 424/406; 424/409; 514/341; 514/531; 523/122
(58) Field of Classification Search .......................... None
See application file for complete search history.

(56) References Cited

U.S. PATENT DOCUMENTS

| | | | |
|---|---|---|---|
| 4,150,109 A | 4/1979 | Dick et al. |
| 4,536,388 A | 8/1985 | Pearce, III et al. |
| 4,543,247 A | 9/1985 | Von Bittera et al. |
| 4,843,068 A | 6/1989 | Hamaguchi et al. |
| 4,879,117 A | 11/1989 | Rombi |
| 5,266,324 A | 11/1993 | Stendel et al. |
| 5,310,557 A | 5/1994 | Brandt et al. |
| 5,437,869 A | 8/1995 | Kelley |
| 5,620,696 A | 4/1997 | Krzewki et al. |
| 5,858,387 A | 1/1999 | Jeannin |
| 5,885,607 A | 3/1999 | Jeannin |
| 6,001,382 A | 12/1999 | Levy et al. |

FOREIGN PATENT DOCUMENTS

| | | |
|---|---|---|
| EP | 0 211 207 A2 | 2/1987 |
| EP | 0 251 472 A2 | 1/1988 |
| EP | 0 537 998 A | 4/1993 |
| EP | 0542078 | 5/1993 |
| EP | 0569791 | 11/1993 |
| EP | 0 576 267 A1 | 12/1993 |
| EP | 0 763 325 A1 | 3/1997 |
| EP | 0 979 605 A1 | 2/2000 |
| EP | 1 289 363 B1 | 6/2004 |
| FR | 2729833 | 8/1996 |
| WO | 95/07615 | 3/1995 |
| WO | 95/33278 | 12/1995 |
| WO | 95/33380 | 12/1995 |
| WO | 00/02453 | 1/2000 |
| WO | 02/49436 A | 6/2002 |
| WO | 02/078443 | 10/2002 |

OTHER PUBLICATIONS

PCT International Search Report dated Oct. 31, 2005, 6 pgs.

*Primary Examiner* — Neil Levy

(57) ABSTRACT

The present invention relates to active compound-containing moulded bodies for external use against parasites on animals.

3 Claims, No Drawings

ACTIVE COMPOUND-CONTAINING SOLID MOULDED BODIES FOR EXTERNAL USE AGAINST PARASITES ON ANIMALS

The present invention relates to active compound-containing moulded bodies for external use against parasites on animals.

Active compound-containing moulded bodies for controlling parasites in animals have been known for a long time. Moulded bodies of this nature are described, for example, in WO 2002/78443, EP-A 539295, EP-A 763325, EP-A 1289363, EP-A 211207, EP-A 124404, EP-A 979605, FR 2729833, U.S. Pat. No. 5,620,696, EP-A 576267, EP-A 569791, EP-A 542078, EP-A 470467, EP-A 251472, EP-A 50782, U.S. Pat. No. 5,858,387 and EP-A 542080. The disadvantage of the previously described processes and mixtures for producing the active compound-containing moulded bodies is that they additionally require the use of phthalic esters, such as dimethyl phthalate and dioctyl phthalate when the conventional polyolefin or vinyl resin matrices are employed (see, for example, WO 01/87065, EP-A-0 211 207 and EP-A-0 569 791). As is known, the phthalates which are used for this purpose and which are serviceable from the technological point of view are not entirely harmless toxicologically. When not properly handled, they can lead to risks in connection with producing and using the moulded bodies and, over and above this, there is the danger of environmental contamination.

It is therefore desirable to replace the said phthalates with environmentally compatible ingredients which are less toxic. These novel ingredients should preferably increase the migration of the active compounds from the polymer matrix, and consequently improve the activity (residual and knockdown effects) of the moulded bodies, without having any negative influence on the good physicochemical properties of the polyolefin matrix.

It has now been found, surprisingly, that this aim can be achieved using particular fatty acid esters of polyhydric alcohols (e.g. di- and triglycerides or propylene glycol esters).

As a result of their physicochemical constitution, these fatty acid esters are polar compounds whereas the said polyolefins and vinyl resins are relatively nonpolar plastics. The skilled person expects polar compounds and nonpolar plastics to be incompatible. In many cases, such combinations lead to demixing/phase separation, in turn leading to substantial impairment of the physicochemical properties of the polymer matrix, such as modulus of elasticity, ductility, tensile stress-elongation and ability to be removed from the given moulding compound, and also to spontaneous migration of the active compound from the plastic matrix and consequently to substantial impairment of the long-term activity. It was therefore surprising that using the said polar fatty esters of polyhydric alcohols does not have a negative influence either on the physicochemical properties or on the long-term activity of the moulded bodies. Contrary to expert opinion, an improvement in processability and long-term action was even observed in many cases.

The invention relates to:
solid moulded bodies for external use against parasites on animals, with the bodies being based on a polyolefin matrix containing
one or more esters composed of a dihydric or trihydric alcohol having up to three carbon atoms and fatty acids having from 6 to 18 carbon atoms
one or more active compounds
and, where appropriate, additional auxiliary substances and additives.

As the alcohol component, the esters which are employed in accordance with the invention contain a dihydric or trihydric alcohol having up to three carbon atoms, such as ethylene glycol, propylene glycol or glycerol. As a rule, at least two, preferably all, of the hydroxyl groups of the alcohol are esterified. The acid component of the esters is constituted by fatty acids which have from 6 to 18 carbon atoms and which can be straight-chain or branched and be monounsaturated or polyunsaturated. It is possible to use mixed esters or mixtures of different ester types. Suitable glycerides are diglycerides and triglycerides, preferably triglycerides, such as, for example, caprylic-capric acid triglycerides or caprylic-capric-linoleic acid triglycerides. Equally preferred are esters composed of propylene glycol and caprylic and/or capric acid (propylene glycol octanoate decanoate). Particularly preferably, these glycerol or propylene glycol esters of caprylic/capric acid have a viscosity range (20° C.) of from 5 to 40, preferably of from 8 to 35, particularly preferably of from 9 to 13 mPa·s. These esters can be obtained from Sasol Germany GmbH/Witten under the trade names Miglyol 840 (propylene glycol octanoate decanoate, CAS No. 68583-51-7) and Miglyol 812 (caprylic-capric acid triglycerides, CAS No. 73398-61-5). It is likewise possible to use their polyethylene oxide-, polypropylene oxide- and/or propylene carbonate-modified derivatives which have the abovementioned viscosity range.

The moulded bodies according to the invention contain the fatty acid esters in proportions of from 1 to 25% by weight, preferably of from 5 to 17.5% by weight, particularly preferably of from 5 to 12.5% by weight (based on the given total mass of the mix).

The solid moulded bodies according to the invention are, for example, neck collars, pendants for neck collars (medallions), ear tags, collars for attachment to limbs or body parts, adhesive strips and films or stripping films. Particular preference is given to medallions and, in particular, neck collars.

Thermoplastic and flexible thermoplastic polyolefins and elastomers are suitable for use as carrier substance or basis for the moulded bodies. Those which may be mentioned are polyvinyl resins, EPDM (ethylene-/propylene-diene terpolymer), polyethylene (e.g. HDPE or LLDPE) and polypropylene, which are sufficiently compatible with the abovementioned active compounds.

The polymers must possess sufficient strength and pliability to ensure that they do not rupture or become brittle during moulding. They must be of adequate durability to be resistant to normal wear and tear. In addition, the polymers must allow adequate migration of the active compound to the surface of the moulded body.

The polyvinyl resins include polyvinyl halides, such as polyvinyl chloride, polyvinyl chloride-vinyl acetate and polyvinyl fluoride; polyvinylbenzenes, such as polystyrene and polyvinyltoluene.

Other plastics which are suitable for use as matrix for the moulded bodies according to the invention are thermoplastic elastomers. These are materials which contain elastomeric phases which are either physically incorporated or chemically bonded in thermoplastically processable polymers. A distinction is made from polymer blends, in which the elastomeric phases are a component of the polymeric skeleton. As a result of the constitution of the thermoplastic elastomers, hard and soft regions are present alongside each other. In this connection, the hard regions form a crystalline reticular structure or a continuous phase whose interstices are filled with elastomeric segments. Because of this constitution, these materials have rubber-like properties. In this connection, reference may be made to thermoplastic polyolefins (TPO) and to styrene block copolymers (see, for example, EP 542078).

According to the invention, preference is given to polyvinyl chloride, polypropylene, polyethylene and EPDM; very particular preference is given to polyvinyl chloride.

In particular cases, customary plasticizers which are known to be used for softening solid vinyl resins can additionally be employed for producing the moulded bodies based on polyolefins, in particular polyvinyl resins. The plasticizer to be used depends on the resin and on its compatibility with the plasticizer. Examples of suitable additional plasticizers are phosphoric acid esters and adipic acid esters, such as diiso- and n-butyl adipate for example. It is also possible to use other esters, such as the esters of azelaic acid, maleic acid, ricinoleic acid, myristic acid, palmitic acid, oleic acid, sebacic acid, stearic acid and trimellitic acid, as well as complex linear polyesters, polymeric plasticizers and epoxidized soybean oils.

Additional plasticizers are, where appropriate, employed in quantities of from about 5 to 50% by weight, preferably of from about 15 to 45% by weight, of the total composition.

It is also possible for the moulded bodies to contain other customary constituents such as stabilizers, lubricants, mould-release agents, fillers and colouring materials; as a rule, these constituents do not significantly alter the fundamental properties of the composition.

Suitable stabilizers are antioxidants and agents which protect the collars from ultraviolet radiation and undesirable breakdown during the processing, such as extruding. Some stabilizers, such as epoxidized soybean oils, also serve as secondary plasticizers.

Examples of lubricants which can be used are stearates, stearic acid and low molecular weight polyethylenes. These constituents are customarily used at a concentration of up to about 5% by weight of the total composition.

When the moulded bodies are produced, the different constituents are mixed in accordance with known methods and moulded in accordance with known extrusion and injection moulding methods.

The choice of the processing method for producing the moulded bodies depends technically in principle on the rheological properties of the polymeric carrier material and on the shape of the desired moulded body. The processing methods can be categorized in accordance with the processing technology or in accordance with the nature of the profiling. In the case of processing technology, the methods can be divided in accordance with the rheological states which are passed through in these methods. Accordingly, casting, pressing injection-moulding and spreading come into consideration for viscous polymeric carrier materials while injection-moulding, extruding, calendering, rolling and, where appropriate, kneading come into consideration in the case of elastoviscous polymers. Classified in accordance with the nature of the profiling, the moulded bodies according to the invention can be produced by casting, dipping, pressing, injection-moulding, extruding, calendering, stamping, bending, thermoforming, etc. Coating of solid basal supports also comes into consideration.

These processing methods are known per se and do not require any more detailed explanation. In principle, the explanations which have been given above for polyvinyl resins, by way of example, apply to other polymers.

While being advantageous from the point of view of homeotherm toxicity, the solid moulded bodies according to the invention are suitable for controlling parasites which are found in animal husbandry and animal breeding in the case of domestic animals and productive animals as well as in the case of zoological animals, laboratory animals, experimental animals and hobby animals. They are effective against normally sensitive and resistant species as well as against all or some of the development stages of the said animals.

Parasites are, in particular, arthropods. Preference is given to using the solid formulations according to the invention for controlling ectoparasites.

The abovementioned ectoparasites include: izodid ticks, argasid ticks, mange mites, harvest mites, flies (biting and licking), parasitizing fly larvae, lice, Trichodecetes lice and Felicola lice, bonomiella lice, ticks and fleas. These parasites include:

From the order of the Anoplurida e.g. *Haematopinus* spp., *Linognathus* spp., *Pediculus* spp., *Phtirus* spp., *Solenopotes* spp.

From the order of the Mallophagida and the suborders Amblycerina and Ischnocerina e.g. *Trimenopon* spp., *Menopon* spp., *Trinoton* spp., *Bovicola* spp., *Werneckiella* spp., *Lepikentron* spp., *Trichodectes* spp., *Felicola* spp.

From the order Diptera and the suborders Nematocerina and Brachycerina e.g. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp. *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida e.g. *Pulex* spp., *Ctenocephalides* spp., *Xenopsylla* spp., *Ceratophyllus* spp.

From the order of the Heteropterida e.g. *Cimex* spp., *Triatoma* spp., *Rhodnius* spp., *Panstrongylus* spp.

From the order of the Blattarida e.g. *Blatta orientalis, Periplaneta americana, Blattella germanica, Supella* spp.

From the subclass of the Acaria (Acarida) and the orders of the meta- and mesostigmata e.g. *Argas* spp., *Ornidthodorus* spp., *Otobius* spp., *Ixodes* spp., *Ixodes Holocyclus, Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata) e.g., *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The moulded bodies are generally suitable for controlling parasites in most animal species, preferably in homeotherms, in particular mammals. The productive and breeding animals include mammals such as cattle, horses, sheep, pigs, goats, camels, water buffalo, donkeys, rabbits, fallow deer and reindeer; fur animals such as mink, chinchilla and raccoon; poultry, such as hens, geese, turkeys and ducks.

The laboratory and experimental animals include cattle, mice, rats, guinea pigs, golden hamsters, dogs and cats.

The hobby animals include horses, dogs, cats, mice, rats, guinea pigs, golden hamsters, hares and rabbits.

The compositions according to the invention are suitable, in particular, for treating cattle, dogs and cats, preferably for controlling ticks and/or fleas.

The compositions can be used either prophylactically or therapeutically.

The moulded bodies customarily comprise the active compound at concentrations of in each case from 0.1 to 30% by weight, preferably of from 1 to 20% by weight, particularly preferably of from 2 to 15.0% by weight, based on the total mass of the solid formulation.

The moulded bodies customarily comprise active compound combinations at total concentrations of from 1 to 35% by weight, preferably of from 2 to 25% by weight, particularly preferably of from 2.5 to 17.5% by weight, based on the total mass of the solid formulation.

The novel solid moulded bodies can comprise active compounds, such as insecticides, acaricides, attractants, sterilizing agents, bacteriocides, nematocides, fungicides, etc. The insecticides, acaricides and growth inhibitors include, for example, phosphoric acid esters, carbamates, carboxylic acid esters, synthetic or natural pyrethroids, neonicotinoids (also termed chloronicotinyls; these include, for example, chloropyridine, chlorothiazole and tetrahydrofuran compounds), pyroximates, phenyl ethers, phenyl ureas, substances produced by microorganisms, and others.

The following are examples of advantageous active compounds and co-active compounds:

Insecticides/Acaricides/Nematocides/Growth Inhibitors:

Abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, Cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, Deltamethrin, demeton M, demeton S, demeton-S-methyl, diafenthiuron, diazinon, dichlorvos, diflubenzuron, dimethoate, dimethylvinphos, diofenolan, disulfoton, docusatsodium, dofenapyn, Eflusilanate, emamectin, empenthrin, endosulfan, *Entomopfthora* spp., eprinomectin, esfenvalerate, ethiofencarb, ethion, ethoprophos, etofenprox, etoxazole, etrimfos, Fenamiphos, fenazaquin, fenbutatin oxide, fenitrothion, fenothiocarb, fenoxacrim, fenoxycarb, fenpropathrin, fenpyrad, fenpyrithrin, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, Granulosis Viruses Halofenozide, HCH, heptenophos, hexaflumuron, hexythiazox, hydroprene, Imidacloprid, isazofos, isofenphos, isoxathion, ivermectin, Nuclear polyhedrosis viruses Lambdacyhalothrin, lufenuron Malathion, mecarbam, metaldehyde, methamidophos, *Metharhizium anisopliae, Metharhizium flavoviride,* methidathion, methiocarb, methomyl, methoxyfenozide, metolcarb, metoxadiazone, mevinphos, milbemectin, monocrotophos, moxidectin, Naled, nitenpyram, nithiazine, novaluron Omethoate, oxamyl, oxydemethon M Paecilomyces fumosoroseus, parathion A, parathion. M, permethin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, Quinalphos, Ribavirin Salithion, sebufos, selamectin, silafluofen, spinosad, sulfotep, silprofos, Taufluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, Ti 435, tralocythrin, tralomethrin, triarathene, triazamate, triazophos, triazuron, trichlophenidine, trichlorfon, triflumuron, trimethacarb, Vamidothion, vaniliprole, *Verticcilium lecanii*

YI 5302

YRC 2894

Zetacypermethrin, zolaprofos (1R-cis)-[5-(Phenylmethyl)-3-furanyl]methyl-3-[(dihydro-2-oxo-3(2H)-furanylidene)methyl]-2,2-dimethylcyclopropanecarboxylate (3-Phenoxyphenyl)methyl-2,2,3,3-etramethylcyclopropanecarboxylate 1-[(2-Chloro-5-thiazolyl)methyl]tetrahydro-3,5-dimethyl-N-nitro-1,3,5-triazin-2(1H)imine 2-(2-Chloro-6-fluorophenyl)-4-[4-(1,1-dimethylethyl)phenyl]4,5-dihydrooxazole 2-(Acetyloxy)-3-dodecyl-1,4-naphthalenedione 2-Chloro-N-[[[4-(1-phenylethoxy)phenyl]amino]carbonyl] benzamide 2-Chloro-N-[[[4-(2,2-dichloro-1,1-difluoroethoxy)phenyl] amino]carbonyl]benzamide 3-Methylphenylpropylcarbamate 4-[4-(4-Ethoxyphenyl)-4-methylpentyl]-1-fluoro-2-phenoxybenzene 4-Chloro-2-(1,1-dimethylethyl)-5-[[2-(2,6-dimethyl-4-phenoxyphenoxy)ethyl]thio]-3(2H)pyridazinone 4-Chloro-2-(2-chloro-2-methylpropyl)-5-[(6-iodo-3-pyridinyl)methoxy]-3(2H)-pyridazinone 4-Chloro-5-[(6-chloro-3-pyridinyl)methoxy]-2-(3,4-dichlorophenyl)-3 (2H)-pyridazinone

*Bacillus thuringiensis* stain EG-2348

Benzoic acid [2-benzoyl-1-(1,1-dimethylethyl)]hydrazide 2,2-Dimethyl-3-(2,4-dichlorophenyl)-2-oxo-1-oxaspiro[4.5] dec-3-en-4-yl butanoate

[3-[(6-Chloro-3-pyridinyl)methyl]-2-thiazolidinylidene]cyanamide

Dihydro-2-(nitromethylene)-2H-1,3-thiazine-3(4H)carboxaldehyde

Ethyl-[2-[[1,6-dihydro-6-oxo-1-(phenylmethyl)-4-pyridazinyl]oxy]ethyl]carbamate

N-(3,4,4-Trifluoro-1-oxo-3-butenyl)glycine

N-(4-Chlorophenyl)-3-[4-(difluoromethoxy)phenyl]-4,5 diyhdro-4-phenyl-1H-pyrazole-1-carboxamide N-[(2-Chloro-5-thiazolyl)methyl]-N'-methyl-N"-nitroguanidine N-Methyl-N'-(1-methyl-2-propenyl)-1,2-hydrazinedicarbothioamide N-Methyl-N'-2-propenyl-1,2-hydrazinedicarbothioamide O,O-Diethyl-[2-[(dipropylamino)-2-oxoethyl]ethylphosphoramidothioate Preferred pyrethroids are cyfluthrin, β-cyfluthrin and flumethrin.

Preferred neonicotinoids (chloronicotinyls) are:

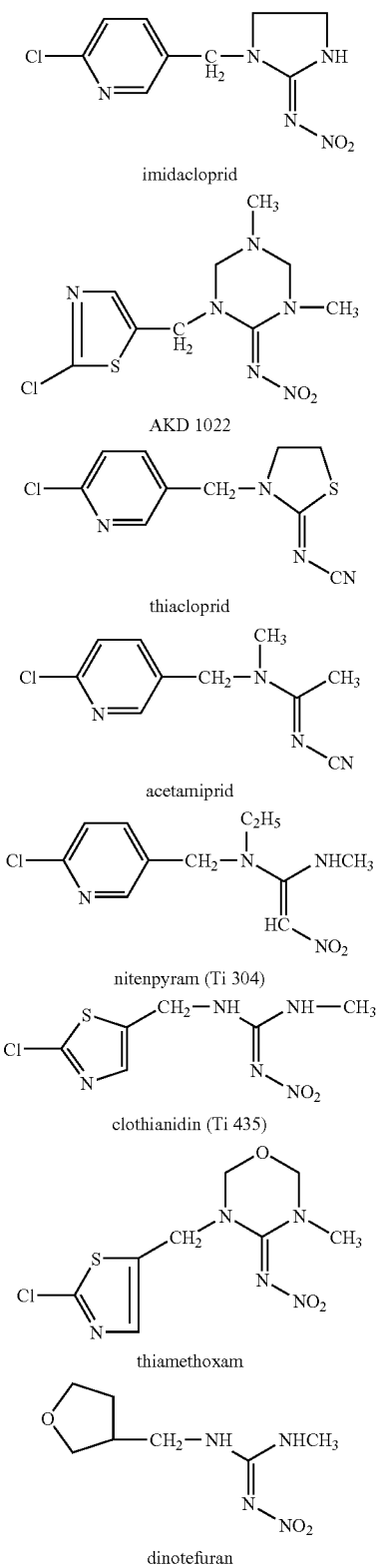

Imidacloprid, thiacloprid, acetamiprid and nitenpyram are representatives of the chloropyridine neonicotinoids; thiamethoxam, clothianidin and AKD 1022 are representatives of the chlorothiazole neonicotinoids and dinotefuran is a representative of the tetrahydrofuran neonicotinoids.

Propoxur may be mentioned as another preferred insecticide.

Preferred growth inhibitors are pyriproxyfen, methoprene and triflumuron; they are suitable, in particular, for use in combination with another insecticide/acaricide.

A preferred synergist is piperonyl butoxide; the synergists are naturally also employed in combination with corresponding active compounds.

The use of the said co-active compounds and synergists together with the said active compounds has in principle been disclosed, see, e.g., WO 00/02453, WO 95/33380, WO 95/07615, EPA 569791, EPA 0736252, EP-A 470461 and EP-A 251472.

Other active compounds which may be mentioned are pyrazole oximes and benzoyl ureas.

Suitable pyrazole oximes having an insecticidal and acaricidal effect are described, for example, in EP-A-0 234 045, which is hereby expressly incorporated by reference.

The benzoyl ureas include compounds of the formula (I):

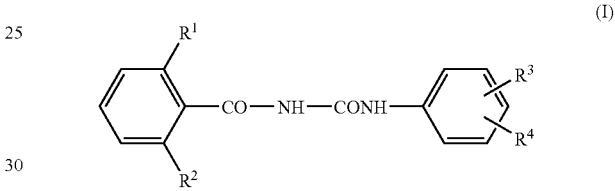

where
$R^1$ is halogen,
$R^2$ is hydrogen or halogen,
$R^3$ is hydrogen, halogen or $C_{1-4}$-alkyl,
$R^4$ is halogen, 1-5-halogen-$C_{1-4}$-alkyl, $C_{1-4}$-alkoxy, 1-5-halogen-$C_{1-4}$-alkoxy, $C_{1-4}$-alkylthio, 1-5-halogen-$C_{1-4}$-alkylthio, phenoxy or pyridyloxy which can be optionally substituted by halogen, $C_{1-4}$-alkyl, 1-5-halogen-$C_{1-4}$-alkyl, $C_{1-4}$-alkoxy, 1-5-halogen-$C_{1-4}$-alkoxy, $C_{1-4}$-alkylthio, or 1-5-halogen-$C_1$-$C_4$-alkylthio.

The said compounds can, in dependence on the substitution pattern, exist in stereoisomeric forms which either relate to each other as image and mirror image (enantiomers) or do not relate to each other as image and mirror image (diastereomers). The invention relates to the enantiomers or diastereomers and also to their respective mixtures. The racemates, as well as the diastereomers, can be separated in a known mariner into the stereoisomerically homogeneous constituents.

In addition, certain compounds can be present in tautomeric forms. This is known to the skilled person and these compounds are likewise encompassed by the scope of the invention.

Where appropriate, the compounds according to the invention can be present either as cis isomers or as trans isomers. Even when only one of the isomers is depicted, it is always the cis isomer and the trans isomer which are meant according to the invention.

The moulded bodies according to the invention are outstandingly suitable for performing external or dermal treatments on animals, in particular dogs, cats and cattle. They usually have a thickness of 0.25-3.5 mm, preferably 0.75-2.5 mm. They are distinguished by their quite outstanding storage stability of 3-5 years in all climatic zones. They are furthermore distinguished by their ease of applicability, their very good biological long-term activity of what is usually up to nine months and by their good environmental compatibility, in particular compatibility with bodies of water and compatibility with homeotherms.

EXAMPLES

Example 1

Composition:

| 2-Isopropoxyphenyl-N-methylcarbamate (Propoxur) | 10 g |
|---|---|
| Di-n-butyl adipate | 21 g |
| Propylene glycol octanoate decanoate (trade name: Miglyol 840, from Sasol/Witten) | 9 g |
| Epoxidized soybean oil | 2 g |
| Stearic acid | 1 g |
| PVC | 56 g |
| Pigment mixture | 1 g |

Preparation: The mixture composed of 2-isopropoxyphenyl-N-methylcarbamate, pigment mixture and PVC is mixed in a mixer together with the mixture composed of di-n-butyl adipate, propylene glycol octanoate decanoate and epoxidized soybean oil. The mixing is continued, while supplying heat, until the mixture is homogeneous. The heating promotes the drawing of the plasticizer mixture into the PVC. After the stearic acid has been subsequently dispersed homogeneously, the mixture is shaped into neck collars by injection moulding.

Example 2

Composition:

| 2-Isopropoxyphenyl-N-methylcarbamate | 10 g |
|---|---|
| Flumethrin | 2.5 g |
| Di-n-butyl adipate | 21 g |
| Propylene glycol octanoate decanoate | 9 g |
| Epoxidized soybean oil | 2 g |
| Stearic acid | 1 g |
| PVC | 54 g |
| Pigment mixture | 0.5 g |

Preparation: The mixture composed of 2-isopropoxyphenyl-N-methylcarbamate, pigment mixture and PVC is mixed in a mixer together with the mixture composed of di-n-butyl adipate, propylene glycol octanoate decanoate, epoxidized soybean oil and flumethrin. The mixing is continued, while supplying heat, until the mixture is homogeneous. The heating promotes the drawing of the active compound-plasticizer mixture into the PVC. After the stearic acid has subsequently been dispersed homogeneously, the mixture is shaped into neck collars by injection moulding. The same mixture is extruded in an extruder to form continuous webs or sheets which are fabricated by the manufacturer or user to a length which is appropriate to the application form. Moulded bodies, which are hung close to the animal in a medallion form, are cut or punched from the extrudate.

Example 3

Composition:

| Flumethrin | 2.5 g |
|---|---|
| Di-n-butyl adipate | 21 g |
| Propylene glycol octanoate decanoate | 9 g |
| Epoxidized soybean oil | 2 g |
| Stearic acid | 1 g |
| PVC | 64 g |
| Pigment mixture | 0.5 g |

Preparation:

The mixture composed of pigment mixture and PVC is mixed in a mixer together with the mixture composed of di-n-butyl adipate, propylene glycol octanoate decanoate, epoxidized soybean oil and flumethrin. The mixing is continued, while supplying heat, until the mixture is homogeneous. The heating promotes the drawing of the active compound-plasticizer mixture into the PVC. After the stearic acid has subsequently been dispersed homogeneously, the mixture is extruded to form continuous webs and sheets which are fabricated by the manufacturer or user to a length which is appropriate to the application form. Moulded bodies, which are hung close to the animal in a medallion or ear tag form, are cut or punched from the extrudate.

Example 4

Composition:

| Imidacloprid | 10 g |
|---|---|
| Flumethrin | 5 g |
| Di-n-butyl adipate | 21 g |
| Propylene glycol octanoate decanoate | 9 g |
| Epoxidized soybean oil | 2 g |
| Stearic acid | 1 g |
| PVC | 51 g |
| Pigment mixture | 1 g |

Preparation: The mixture composed of imidacloprid, pigment mixture and PVC is mixed in a mixer together with the mixture composed of di-n-butyl adipate, propylene glycol octanoate decanoate, epoxidized soybean oil and flumethrin. The mixing is continued, while supplying heat, until the mixture is homogeneous. The heating promotes the drawing of the active compound-plasticizer mixture into the PVC. After the stearic acid has subsequently been dispersed homogeneously, the mixture is shaped into neck collars and medallions by injection moulding.

The pigment mixtures mentioned in the examples are a mixture of commercially available iron oxides in the case of Examples 1 and 4 and a mixture of commercially available titanium dioxide and iron oxide in the case of Examples 2 and 3.

Activity Experiments

In order to carry out experiments determining activity against fleas and ticks, dogs were treated with neck collars, or cattle were treated with an extrudate which was adapted to their body size, in accordance with Examples 1, 2, 3 or 4. The treatment took place by means of a moulded body being attached to the neck of the animals in the form of a neck collar (strip of approx. 1.4 cm in width). The strips were fitted as close as possible (with a finger-width's gap) to the necks of the animals. Medallions were perforated and attached to a conventional, active compound-free neck collar. The medallion was located such that it was in contact with the coat of the animal in the anterior neck region.

Example A

Activity Against Fleas (*Ctenocephalides felis*) in Dogs

On days -4 and -1, dogs are infested with approx. 100 adult, fasting *Ctenocephalides felis* per dog. These fleas are applied to the neck of the animal.

On day 0, the success on the infestation is examined in the dog by looking for fleas on the conscious animal. The number of live fleas is recorded.

After the fleas have been counted, the animals are treated. The dogs in the control group are not treated. The pharmaceuticals to be examined are administered to the animals as a neck collar or as a medallion. Neck collars and medallions remain on the animals until the end of the experiment on day 170. In each case, only 1 neck collar or 1 medallion is administered per animal. Only clinically healthy animals are used.

On day 1 and day 2, all the dogs are examined for live fleas. The results are recorded in the raw data.

On days 14, 28, 56, 84, 112, 140 and 168 all the dogs are reinfested with approx. 100 adult, fasting *Ctenocephalides felis* per dog. All the dogs are checked for live fleas in each case one and two days after reinfestation. The results are recorded in the raw data.

A modified formula, adapted from Abbott, is used for calculating the activity:

$$\text{Activity \%} = \frac{\emptyset \text{ number of fleas } CG - \emptyset \text{ number of fleas } TG}{\emptyset \text{ number of fleas } CG} \times 100$$

CG: control group

TG: treatment group

Activities of >90% against *Ctenocephalides felis* over a period of 5-6 months are achieved using the active compound-containing moulded bodies which are produced in accordance with Formulation Examples 1, 2, 3 or 4 and which are administered as neck collars and as medallions.

Example B

Activity Against Ticks (*Ixodes ricinus*) in Dogs

On day -1, dogs are sedated with 2% Rompun® (Bayer AG) (0.1 ml/kg of bodyweight). After all the dogs have been sedated (after approx. 10-15 minutes), they are transferred to transport boxes and 50 *Ixodes ricinus* (25 ♀, 25 ♂) per dog are applied to the neck of the animal. After approx. 1.5 hours, the animals are transferred once again from the transport box into the cage.

On day 0, the success of the infestation is examined on the dog by looking for ticks on the conscious animal. In this connection, a thorough search is conducted in the head and ear region, including the ear fold, in the region of the neck, on the lower abdomen, on the intramammary region, on the lateral flank and also between the toes and on the limbs. The number of live ticks which have attached themselves by suction is recorded. Dead ticks are removed.

After the ticks have been counted, the animals are treated. The dogs in the control group are not treated. The pharmaceuticals to be tested are administered to the animals as neck collars or as medallions. Neck collars and medallions remain on the animal until the end of the experiment on day 170. In each case only 1 neck collar or 1 medallion is administered per animal. Only clinically healthy animals are used.

On day 1 and day 2, all the dogs are examined for live and dead ticks which have attached themselves by suction. The results are recorded in the raw data. On day 2, all the live and dead ticks are removed from the dog.

On days 14, 28, 56, 84, 112, 140 and 168, all the dogs are reinfested with in each case 50 *Ixodes ricinus* (25 ♀, 25 ♂) per dog. In each case one and two days after reinfestation, all the dogs are checked for live and dead ticks which have attached themselves by suction. The results are recorded in the raw data. On 2nd day after reinfestation, all the live and dead ticks are removed from the dog.

A modified formula adapted from Abbott is used for calculating the activity:

$$\text{Activity \%} = \frac{\emptyset \text{ number of ticks } CG - \emptyset \text{ number of ticks } TG}{\emptyset \text{ number of ticks } CG} \times 100$$

CG: control group

TG: treatment group

Activities of >90% against *Ixodes ricinus* over a period of 5-6 months can be achieved using the active compound-containing moulded bodies which are produced in accordance with Formulation. Examples 1, 2, 3 or 4 and which are administered as neck collars and as medallions.

Example C

Activity Against Australian Ticks (*Ixodes holocyclus*) in Cattle

On day -1, cattle are sedated with 2% Rompun® (Bayer AG) (0.1 ml/kg of bodyweight). After all the cattle have been sedated (approx. 10-15 minutes), 10 *Ixodes holocyclus* (5 ♀, 5 ♂) per bovine are applied to the neck of the animal.

On day 0, the success of the infestation is examined on the bovine by looking for ticks on the conscious animal. In this connection, a full search is carried out in the head and ear region including the ear fold, in the region of the neck, on the lower abdomen, on the intramammary region, on the lateral flank and between the toes and on the limbs. The number of live ticks which have attached themselves by suction is recorded. Dead ticks are removed.

After the ticks have been counted, the animals are treated. The cattle in the control group are not treated. The pharmaceuticals to be tested are administered to the animals as a neck collar. Neck collars remain on the animals until the end of the experiment on day 170. In each case, only 1 neck collar is administered per animal. Only clinically healthy animals are used.

On day 1 and day 2, all the cattle are examined for live and dead ticks which have attached themselves by suction. The results are recorded in the raw data. On day 2, all the live and dead ticks are removed from the bovine.

On days 14, 28, 56, 84, 112, 140 and 168, all the cattle are reinfested with in each case 50 *Ixodes holocyclus* (5 ♀, 5 ♂) per bovine. In each case one and two days after reinfestation, all the cattle are checked for live and dead ticks which have attached themselves by suction. The results are recorded in the raw data. On the 2nd day after reinfestation, all the live and dead ticks are removed from the bovine.

A modified formula adapted from Abbott is used for calculating the activity:

$$\text{Activity \%} = \frac{\varnothing \text{ number of ticks } CG - \varnothing \text{ number of ticks } TG}{\varnothing \text{ number of ticks } CG} \times 100$$

$CG$: control group $TG$: treatment group

Activities of >90% against *Ixodes holocyclus* over a period of 5-6 months are achieved using the active compound-containing moulded bodies which are produced in accordance with the Formulation Examples 1, 2, 3 or 4 and which are administered as neck collars.

The invention claimed is:

1. A solid moulded body for external use against parasites on animals, the solid moulded body comprising a mixture of:
   a. Polyvinyl chloride;
   b. Propylene glycol dicaprylocaprate at concentration of from about 5% to about 17.5% by weight of the solid moulded body;
   c. Imidacloprid at concentration of from about 1% to about 20% by weight of the solid moulded body; and,
   d. Flumethrin at concentration of from about 1% to about 20% by weight of the solid moulded body.

2. A method of dermally controlling parasites on an animal comprising contacting the animal with the solid moulded bodies of claim 1.

3. The solid moulded body according to claim 1, further comprising a plasticizer, a stabilizer, a coloring material, or combinations thereof.

* * * * *